United States Patent [19]

Altman et al.

[11] Patent Number: 5,169,785
[45] Date of Patent: Dec. 8, 1992

[54] METHOD FOR DETECTING FUEL DILUTION OF MARINE LUBRICATING OILS

[75] Inventors: Lawrence J. Altman, Cherry Hill; Paul T. Reischman, Lambertville, both of N.J.

[73] Assignee: Mobil Oil Corporation, Fairfax, Va.

[21] Appl. No.: 603,346

[22] Filed: Oct. 26, 1990

[51] Int. Cl.$^5$ ............................................. G01N 24/10
[52] U.S. Cl. ........................................ 436/60; 436/83; 436/173; 324/316; 324/317
[58] Field of Search ................... 436/55, 60, 83, 173; 422/62; 208/50; 324/316, 317

[56] References Cited

U.S. PATENT DOCUMENTS 3,087,888  4/1963  Saraceno .
4,777,140 10/1988  Rudnick .............................. 436/55

OTHER PUBLICATIONS

Nov-85:016192; Moriya-cho et al., "The Characteristics of Metal Complexes Before and After Hydrotreating", Am. Chem. Soc. Div. Pet. Chem. Prepr. (United States) v. 31:2 Apr. 1986, pp. 597-605.
CLA-90: 040802; "ESR Characterization of Phenalenyl Radicals in Various Fuel Samples"; Fuel (UK) v. 69:2 Feb. 1990, pp. 203-206.
Nasirov et al.; "Study and Isolation of Vanadylporphyrins from Petroleums of the Buzachi Peninsula"; Khim. Prir. Soedin. (3) pp. 389-392.
Malhotra et al.; "34 GHZ EPR Study of Vanadyl Complexes in Various Asphallenes, Statistical Correlative Model of the Coordinating Liquids"; Fuel 64(3) pp. 335-341.
Galambos et al.; "ESR Spectra of Vanadium Complexes in Oils"; Magy. Kem. Foly. 79(8) 364-6.
"Association of Vanadium Chelates in Petroleum Asphaltenes as Studied by ESR", Tynan and Yen, *Fuel, 48*, 191 (1969).
"An Electron Paramagnetic Resonance Investigation of Vanadium in Petroleum Oils", Saraceno, Fanale and Coggeshall, *Anal. Chem. 33*, 500 (1961).

*Primary Examiner*—James C. Housel
*Assistant Examiner*—Jeffrey R. Snay
*Attorney, Agent, or Firm*—Alexander J. McKillop; Charles J. Speciale; Malcolm D. Keen

[57] ABSTRACT

Vanadium in marine diesel lubricating oils resulting from raw fuel dilution is detected and quantified by way of an analytical technique employing electron spin resonance (ESR). Dilution of the lubricating oil with residual fuel oils results in the presence of vanadium in the lubricating oil in a form which is capable of being observed by ESR; by contrast, vanadium resulting from the presence of fuel oil combustion products (pentavalent vanadium) in the lubricating oil is not observed by ESR. The method therefore enables fuel vanadium, typically present as vanadyl porphyrins, to be differentiated from vanadium resulting from blow-by in the engine so that the operating condition of the engine may be monitored.

14 Claims, 3 Drawing Sheets

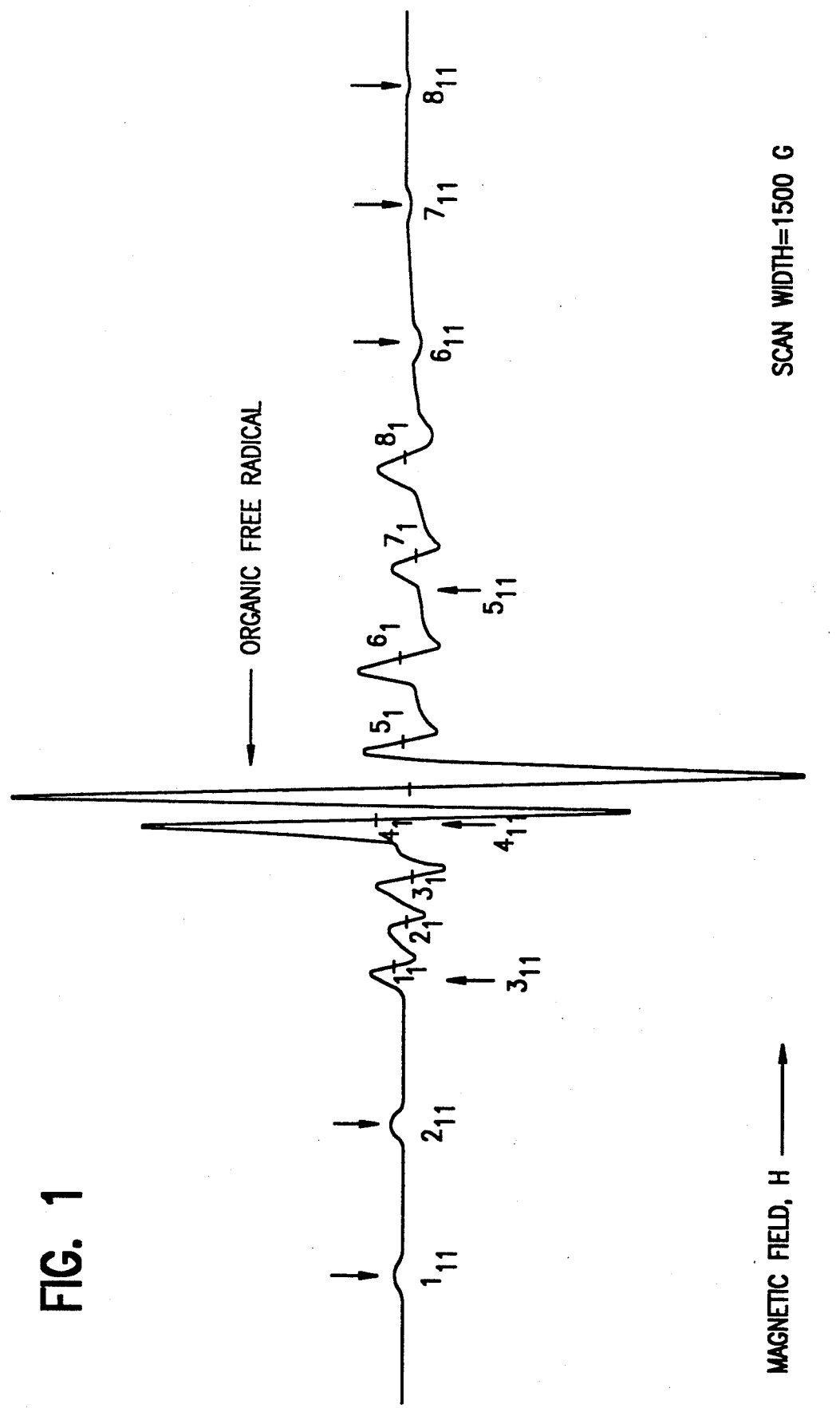

METHOD FOR DETECTING FUEL DILUTION OF MARINE LUBRICATING OILS

FIELD OF THE INVENTION

This invention relates to a rapid analytical method for detecting and quantifying raw fuel dilution of marine lubricating oils, particularly in marine diesel engines burning residual fuels.

BACKGROUND OF THE INVENTION

In recent years diesel engines have been progressively replacing steam turbines in marine vessels, mainly as a result of the improved economics of the marine diesel. Marine diesel engines may generally be classified as slow speed, medium speed or high speed engines with the slow speed variety being used for major, deep draft vessels. Slow speed diesel engines are typically direct coupled, direct reversing, engines operating in the range of 90 to 250 rpm which are usually run on residual fuels. These engines are cross-head construction with a diaphragm and stuffing boxes separating the power cylinders from the crank case to prevent combustion products from entering the crankcase and mixing with the crankcase oil. Medium speed engines typically operate in the range of 250 to 1100 rpm and may operate on the four stroke or two stroke cycle. These engines operate well on intermediate fuel oil (180 cSt at 50° C.) as compared to the heavier marine fuel oil (Bunker C) which is satisfactory for slow speed engines. High speed diesel engines comparable to automotive diesel engines are normally employed in deep draft vessels only for special, ancillary applications and these engines require high quality distillate fuel oil for satisfactory operation although recent developments in engine design have indicated that efficient operation on heavy fuels in feasible.

With low speed marine engines, the cylinders and crank case are lubricated separately, with cylinder lubrication being provided on a once-through basis by means of injection devices which apply cylinder oil to lubricators positioned around the cylinder liner. The crankcase oil provides lubrication for the bearings, gearing, valve gear and other ancillary engine components and is typically an additive type oil selected for good oxidation and thermal stability, water demulsability, corrosion protection and good antifoam performance. Alkaline additives may also be present to neutralize any strong acids entering the crankcase through piston rod glands and detergency and extreme pressure (EP) performance may also be provided by the use of suitable additives. Similar performance characteristics are appropriate for the crankcase oils in residual burning, medium speed engines in which the crankcase oil may also be used, in certain types, for splash cylinder lubrication. Other types of medium speed engines may have separate formed feed cylinder lubrication.

Intermingling of the crankcase oil and cylinder oil is generally unavoidable, particularly in view of the relatively large amounts of crankcase oil which may pass through the piston rod packing gland in large engines. The commingled oil is generally returned to the crankcase even though it may be comtaminated with cylinder oil drainings and blow-by gases. The potential for contamination makes it necessary, however, to monitor the condition of the crankcase oil at frequent intervals to ensure that satisfactory lubricating qualities are maintained.

Two specific problems frequently arising in marine diesel engines are blow-by of combustion products and raw fuel dilution of the lubricating oil. To a certain extent, blow-by is inevitable since some leakage around the piston rings takes place, especially in the larger engine sizes. Fuel dilution may occur when seals in engine ancillaries fail to perform adequately, with the result that the chemical composition of the lubricating oil may be altered and sludge formation accelerated with possible fouling of the engine and failure of major components. Normally, a certain degree of fuel dilution is considered acceptable and in most cases up to about 5% dilution can be tolerated. Frequent monitoring of the engine oil is, however, required to maintain fuel dilution within acceptable levels.

Another problem arising in the lubrication of marine diesel engines is sludge formation. The formation of sludge is obviously undesirable and it is very important to determine the cause of the sludge formation in order to prevent damage to the engine. This is particularly so with expensive marine engines. Sludge may be formed by fuel dilution of the lubricating oil because the lubricating oil is highly paraffinic whereas the fuel oils are rather aromatic materials which may be relatively immiscible with the lubricating oil. Sludges resulting from raw fuel dilution are probably the polar, highly aromatic fraction of the fuel oil called asphaltenes. This fraction should be only partly soluble in the lubricating oil. Finding the cause of the sludge formation is, however, difficult since the current practice is limited to elemental analysis and this is incapable of determining whether the cause of the sludge formation is related to fuel dilution.

So far, no conventional method for detecting fuel dilution of lubricating oils has been considered satisfactory. Viscosity measurements are unreliable. Chemical analysis of the vanadium content of the oil may also be misleading because it is incapable of distinguishing between vanadium derived from fuel dilution and vanadium which may have entered the lubricating oil as a result of blow-by. Although methods designed to separate fuel vanadium from combusted vanadium by extraction have been considered, they are time consuming and yield uncertain results. A need for a rapid analytical method for reliably detecting raw fuel dilution in marine lubricating oil therefore persists.

SUMMARY OF THE INVENTION

We have now discovered that fuel dilution in marine lubricating oil may be rapidly and reliably detected by the use of electron spin resonance (ESR) spectroscopic techniques. ESR is capable of detecting <1 ppm of vanadium, present as the result of fuel dilution in marine oils and is a rapid, reliable technique. The technique takes advantage of the fact that the heavy residual fuels used in marine vessels generally contain at least 50 ppm of vanadium which is present in the fuel in a paramagnetic form, believed to be vanadyl porphyrins, which can be detected and quantified by ESR. Combusted vanadium, however, is in the form of vanadium pentoxide but this compound is diamagnetic and exhibits no ESR spectrum. Thus, ESR is capable of detecting and quantifying vanadium which results exclusively from raw fuel dilution of the lubricating oil.

According to the present invention we therefore provide a method of detecting and quantifying raw fuel dilution of marine diesel lubrication oils by measuring the electron spin resonance (ESR) spectrum of the oil to determine the presence of fuel contaminants in the oil in a form which is ESR active. The preferred technique utilizes the presence of paramagnetic vanadium in he lubricating oil to monitor possible fuel contamination but as an alternative, the organic free radical ESR signal may be used, at least for a qualitative determination of fuel contamination. The percentage of fuel dilution can be quantified by the paramagnetic vanadium content of the oil when the vanadium content of the fuel is known either by ESR measurements or by elemental analysis, provided that this was the only fuel used since the last analysis of the oil. The presence of paramagnetic vanadium—related to dilution of the lubricating oil by raw fuel—can be determined either from the oil itself or from samples of any sludge which may be present in the oil with a positive response to the analysis implying dilution of the lubricating oil by the raw fuel.

DRAWINGS

In the accompanying drawings, FIGS. 1, 2A, 2B and 2C are ESR spectra of fuel oil and lubricating oil samples, as described below in the Examples.

DETAILED DESCRIPTION

Figure 2A:
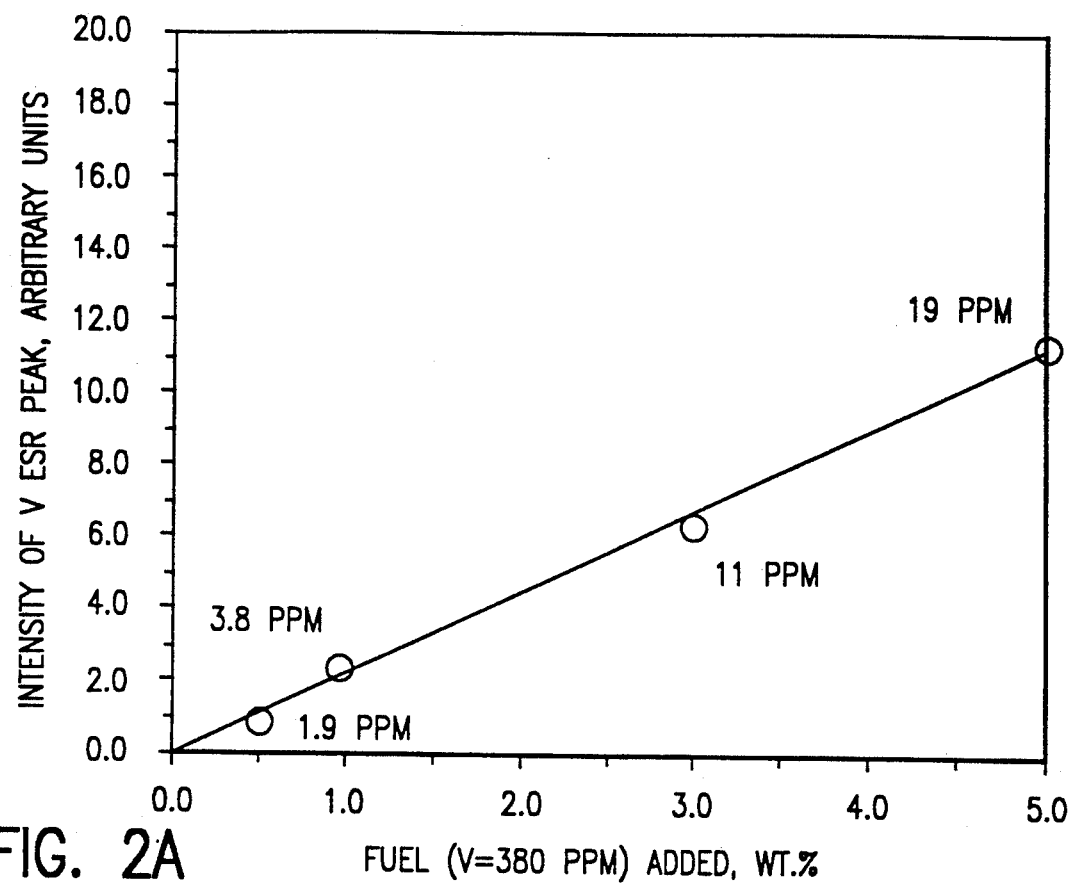

The presence of raw fuel oil in the lubricating oil of marine diesels is determined according to the present invention by ESR analysis of the lubricating oil or of sludge samples removed from the oil. As noted above, the presence of sludge in the lubricating oil may be indicative of fuel dilution in itself although other causes of sludge formation also exist and it is desirable to determine the exact cause of the origins of the sludge. The present method is capable of making a determination whether any sludge in the engine is of fuel origin or whether other causes should be sought. The ESR spectroscopic method is unique in its ability to detect and quantify as little as 1 ppm or less of vanadium (as vanadyl) in either the lubricant or sludge samples separated from the lubricant. If vanadyl is detected in either, dilution of the oil by raw fuel is implicated.

In accordance with the present invention, a sample of a lubricating oil or oil sludge removed from a marine diesel engine is subjected to ESR analysis to determine the presence of vanadium in a paramagnetic form. The lubricating oil may be a marine diesel crankcase oil or cylinder oil, depending upon the analytical needs of the engine. The oil or sludge may be sampled and subjected to ESR analysis in accordance with conventional techniques in which a small sample of the oil or the sludge is positioned in the sample cavity of an ESR spectrometer, for example, in a quartz sample tube. The ESR spectrum is then obtained in the normal way by the application of microwave power to the sample in the presence of a magnetic field. Normally the magnetic field is varied by means of a field modulator while the frequency of the microwave energy is maintained constant in order to detect the resonances of the sample. The ESR spectrum may be any convenient form, according to the type of equipment but is conventionally available as a spectrograph output which plots absorbance as a function of the magnetic field, usually recorded as the first derivative of the absorption to provide for greater resolution of broad lines.

In the present analytical technique, the determination of fuel vanadium may suitably be made at ambient temperature using conventional ESR spectroscopic equipment, for example, equipment operating in the L-band (1.0–1.2 GHz), S-band (4 GHz), X-band (9.1–10.0 GHz) or Q-band (33.5–34.6 GHz), with the field being appropriate in each case to the resonating frequency. Good results have been obtained by operating at ambient temperature with a center field strength of approximately 3.5 kG with a 500–1500 G scan range, operating at a frequency of 9.73 gHz (X-band) with the modulator operating at 100 kHz using a field modulation intensity of 2.0 $G_{pp}$. The present analytical technique is described below with particular reference to the use of the X-band but is generally applicable to operation at other ESR frequencies with suitable adjustment of other operating parameters.

The X-band ESR spectrum of raw fuel in marine lubricating oil is essentially identical to that of residual fuel. The ESR signals for vanadium in patroleum have been identified and labeled by E. C. Tynan and T. F. Yen, Fuel, 48, 191 (1969), using an X-band ESR spectrometer, as two sets of 8 anisotropic peaks. These are shown in the spectrum of a typical residual fuel in FIG. 1. Detecting and quantifying the ESR active vanadium in fuel diluted marine lubricating oil may be made by measuring from the baseline to the top of the positive No. 4 vanadium peak. This peak is the most intense vanadium peak and is generally free of interferences from other peaks in used lubricating oil. However, other peaks or combinations of peaks may also be used, for example, Saraceno (Anal. Chem. 33, 500 (1961); 34, 694 (1962); U.S. Pat. No. 3,087,888) used the sum of the positive No. 4 and the negative No. 3 peaks while Rudnick (U.S. Pat. No. 4,777,140) used the sum of the No. 6 anisotropic and No. 5 isotropic peaks to measure vanadium content in refinery streams. When another microwave frequency is used, for example Q-band, the vanadium spectrum may be sufficiently different to require monitoring other peaks.

In actual used marine lubricating oils, the No. 4 vanadium peak resulting from fuel dilution does occasionally have interferences in the X-band ESR spectrum. Troublesome paramagnetic contaminants include iron, copper and insolubles. Iron contaminants exhibit a very broad peak in the ESR spectrum but generally only cause a baseline shift which is a minor problem. Copper contaminants have ESR signals very close to several vanadium peaks including the No. 4 peak. This interference is particularly troublesome when the vanadium concentration resulting from fuel dilution is <3 ppm. The organic free radical signal is occasionally broadened due to insolubles, probably soot, and can overlap with the vanadium No. 4 peak. In spite of these various interferences, fuel vanadium generally has at least one peak which is free of them, so the vanadium concentration can still be quantified.

The basis upon which the present technique is founded is our discovery that the vanadium which is present in marine diesel fuels, typically heavy residual fuels, is vanadium which may be observed by electron spin resonance. This form of vanadium, which therefore contains an unpaired electron, is believed to be present in the form of vanadyl porphyrins or vanadyl bonded to porphyrin-like ligands, originating in the high boiling or non-distillable fractions of the original crude oil. By contrast, the vanadium which is present in the combustion products of the fuel (referred to here as "combusted vanadium") is in the form of vanadium pentoxide which has only paired electrons and is therefore not observable by ESR. The use of ESR is therefore capable of differentiating between vanadium which is present in the lubricating oil as a result of fuel dilution and vanadium which may result from the normal blow-by in the engine. If the present analytical technique is combined with a conventional chemical analysis for total vanadium, the relative contributions of fuel dilution and blow-by to the total vanadium content may be determined. In addition, the percentage of fuel dilution may be calculated if the vanadium content of the fuel is known and has not changed significantly since the last time the oil was analyzed.

FIG. 1 shows a typical ESR spectrum of a marine heavy fuel (residual) suitable for use in a slow speed marine diesel. The most intense peak (g=2.003) rises from the presence of organic free radicals in the fuel which exhibits strong absorbance in the ESR region. All other peaks in the spectrum are the anisotropic and isotropic vanadium peaks. By contrast, typical new marine lubrication oils show no vanadium peaks and only a weak, if any, free radical peak near g=2.003 due to additives.

When the lubricating oil becomes diluted with fuel, the vanadium from the fuel can be readily detected by ESR as it exhibits its characteristic absorption peaks. By contrast, the pentavalent vanadium arising from the presence of fuel combustion products in the lubricating oil is not ESR active and is not observed. Quantitatively, the percentage of fuel in the lubricating oil can be determined by measuring the intensities of the vanadium peaks which can then be referred to a calibration function generated by making initial measurements of the peak intensities of reference samples. A number of references are available but the preferred reference is vanadyl etioporphyrin, one of the predominant vanadium compounds believed to be in petroleum, dissolved in a new marine lubricating oil with its vanadium concentration determined by elemental analysis.

In principle, the organic free radical signal of the fuel could also be used to monitor fuel dilution of marine lubrication oils. However in practice, it serves only as a secondary indicator. The problem is that this signal overlaps with the free radical signal from certain oil additives and it can overlap with organic free radicals which can arise from several sources including oxidation of the oil and soot contaminants. As a result, the organic free radical signal in used marine lubrication oils may have contributions from several sources including fuel, so the fuel contribution cannot be reliably quantified. A very intense organic free radical signal in used lubrication oils does, however, indicate the probable presence of raw fuel in the oil.

If the analysis is to be carried out on a sample of a sludge removed from from the engine, it may be necessary to dissolve the sludge in a solvent such as toluene if the sludge is too viscous for easy handling or for obtaining the ESR spectrum. For quantitative determinations with sludge samples, the sludge may be weighed out and dissolved in the solvent following which the paramagnetic vanadium content determined from the dissolved sample and compared to a suitable reference such as vanadium ethioporphyrin dissolved in the same solvent as the sludge sample.

Sludge may, of course, form as a result of oil oxidation or from other causes such as combusted fuel contamination but these other factors are unlikely to imply the presence of ESR active vanadium. Combustion products may contain $V_2O_5$ which, as noted above, is inactive to ESR. In this case, elemental analysis is important, particularly when compared to the ESR analysis. Since oxidation of the oil may also result in the formation of sludges there is a possibility that vanadyl in the oil arising from fuel contamination could be oxidized under normal operating conditions to an ESR inactive form. This, however, is unlikely since it is known that petroleum residua can be heated in air to at least 100° C. without affecting the vanadyl concentration; furthermore, the ability to detect vanadyl in samples of used marine oils indicates that vanadyl is capable of surviving under normal engine operating conditions.

The following Examples illustrate the present invention and demonstrate that the vanadyl concentration in new and used marine lubricating oils may be rapidly quantified by the use of ESR analysis.

EXAMPLE 1

A residual fuel containing 380 ppm V was added to a fresh marine diesel lubricating oil (Mobilgard 424, trademark) in weight percentages of 0.5%, 1%, 3%, and 5%, corresponding to vanadium contents of 1.9 ppm, 3.8 ppm, 11 ppm and 19 ppm in he lubricating oil. The intensities of the positive number 4 vanadium peak in the ESR spectra (data acquisition time for each sample, 50 sec) are plotted in FIG. 2A and show that the intensities of the ESR peaks are directly proportional to the vanadium content.

EXAMPLE 2

Figure 2B:
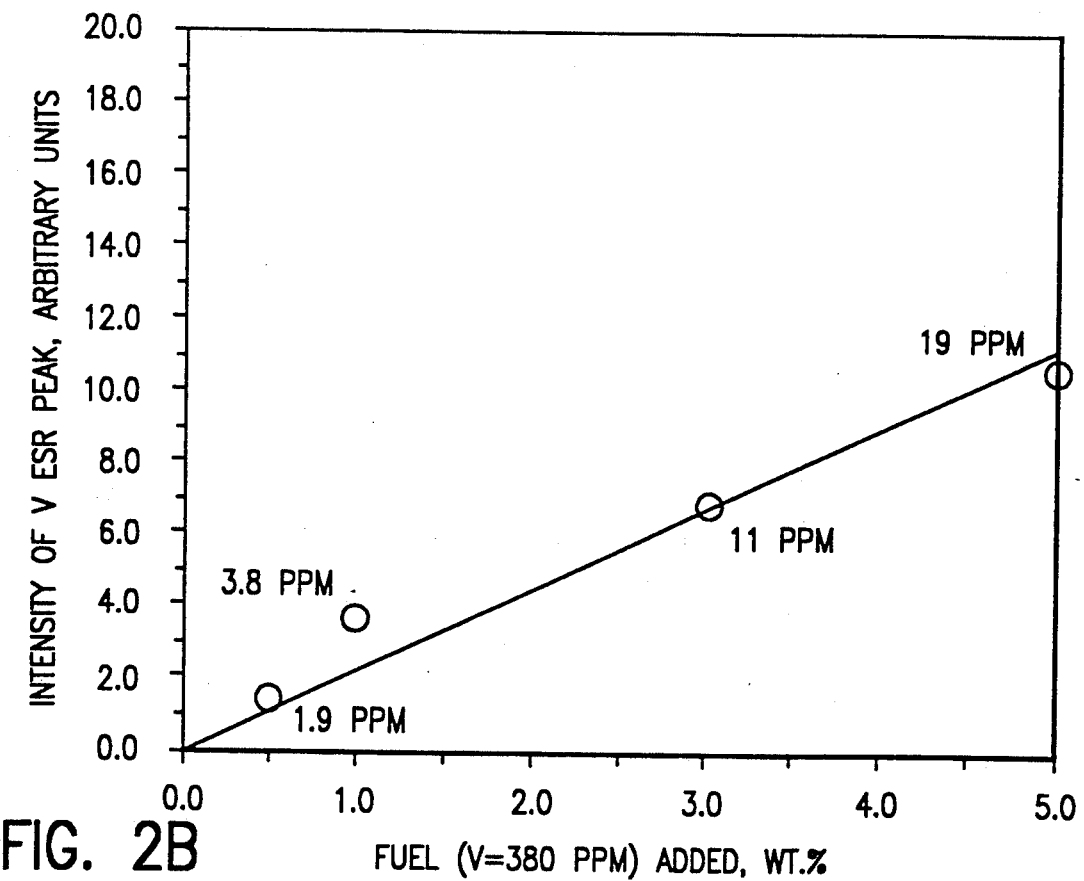

A residual fuel containing 380 ppm V was added to a used marine diesel lubricating oil (Mobilgard 300, trademark, low V, low Fe) in weight percentages of 0.5%, 1.0%, 3.0% and 5.0%. The intensities of the positive number 4 vanadium peak in the ESR spectra (data acquisition for each sample, 50 sec.) are plotted in FIG. 2B. The data show a linear relationship between the peak intensities and the fuel vanadium content ranging from 0 to 19 ppm V.

EXAMPLE 3

Figure 2C:
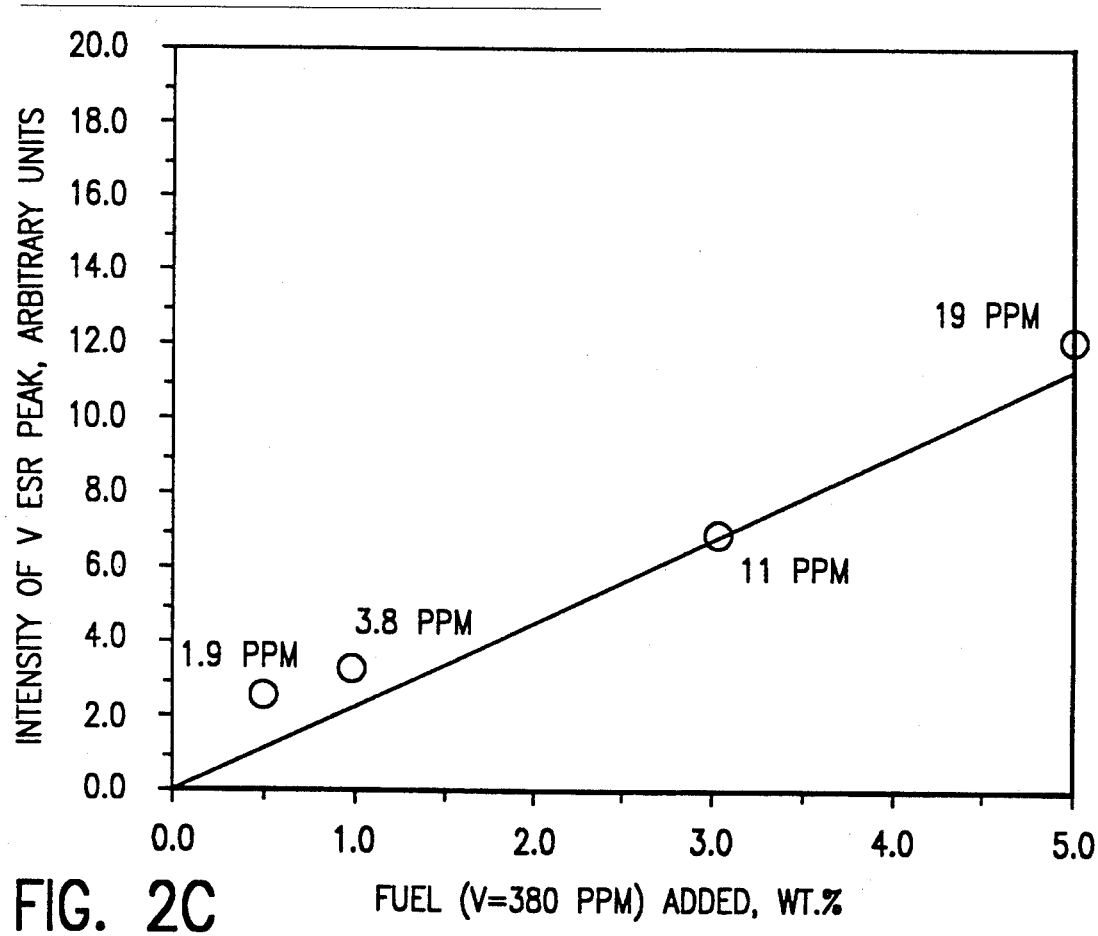

A residual fuel containing 380 ppm V was added to a used marine diesel lubricating oil (Mobilgard 24, trademark, low V, low Fe) in weight percentages of 0.5%, 1.0%, 3.0% and 5.0%. The intensities of the positive number 4 vanadium peak in the ESR spectra (data acquisition time 50 sec) are plotted in FIG. 2C. The data are reasonably linear from 0 to 19 ppm of fuel vanadium.

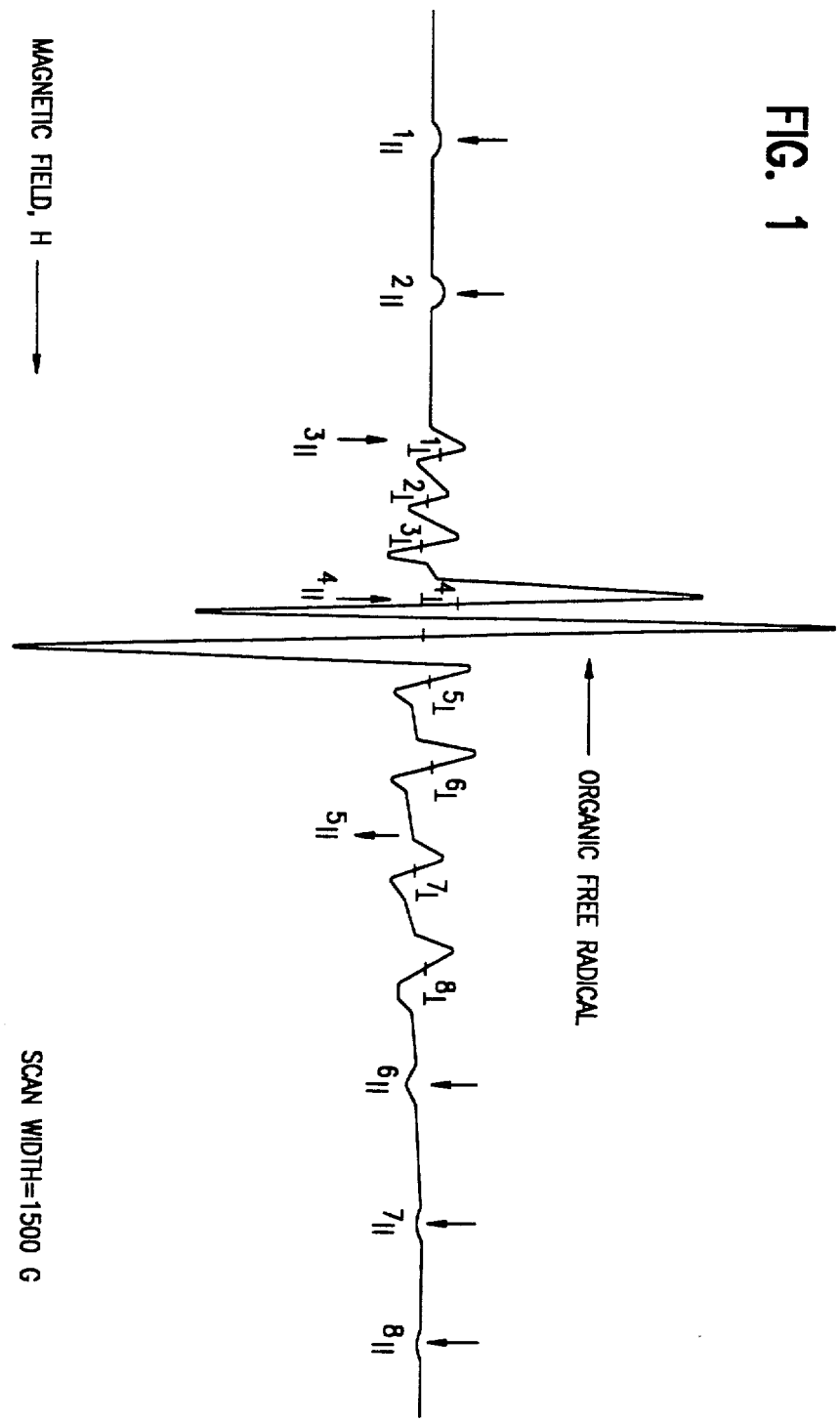

We claim:

1. A method for detecting resid fuel dilution in marine diesel lubricating oils which comprises subjecting a sample of a used marine diesel lubricating oil to ESR analysis and determining the presence of paramagnetic vanadium by reference to an ESR absorption peak which is observed in the ESR spectrum and comparing the paramagnetic vanadium content determined by reference to the ESR absorption peak with the total vanadium content.

2. A method according to claim 1 in which the presence of paramagnetic vanadium is determined from the positive number 4 vanadium peak in the ESR spectrum.

3. A method according to claim 1 in which the lubrication oil is subjected to the ESR analysis using a data acquisition time of not more than 60 seconds.

4. A method of indicating fuel dilution by differentiating between vanadium present in a sample of a marine diesel lubricating oil arising from resid fuel dilution and from the presence of diesel fuel combustion products in the lubricating oil, which comprises measuring the ESR spectrum of a sample of the lubricating oil representative of the presence of paramagnetic vanadium in the oil, and comparing the paramagnetic vanadium content determined by reference to the ESR spectrum with the total vanadium content to provide an indication of the fuel dilution.

5. A method according to claim 4 in which the paramagnetic vanadium is present as vanadyl porphyrins.

6. A method according to claim 4 in which the lubrication oil is subjected to the ESR analysis using a data acquisition time of not more than 60 seconds.

7. A method according to claim 4 in which the presence of paramagnetic vanadium is determined from a vanadium ESR absorption peak in the ESR spectrum.

8. A method according to claim 7 in which the ESR spectrum is determined at the positive number 4 vanadium peak.

9. A method according to claim 8 in which the ESR spectrum is determined in the X-band at the positive number 4 vanadium peak.

10. A method of making a quantitative determination of the amount of vanadium resulting from resid fuel dilution in a sample of a used marine diesel lubricating oil, which comprises:

measuring the intensity of at least one selected ESR absorption peak in the ESR spectrum of reference samples of a lubricating oil having known paramagnetic vanadium contents, preparing a calibration relating the paramagnetic vanadium contents of the reference samples as a function of the intensity of the selected spectral peak for each reference sample, measuring the intensity of the selected spectral peak of the ESR absorbence of a sample of the used marine diesel lubricating oil having an unknown vanadium content and determining the paramagnetic vanadium content of the sample of the used oil from the calibration function and comparing the paramagnetic vanadium content determined by reference to the ESR absorption peak with the total vanadium content.

11. A method according to claim 10 in which the presence of paramagnetic vanadium is determined from a vanadium ESR absorption peak in the ESR spectrum.

12. A method according to claim 10 in which the total vanadium content is determined by chemical analysis.

13. A method according to claim 10 in which the selected peak is the number 4 vanadium peak in the ESR spectrum.

14. A method according to claim 13 in which the ESR spectrum is determined in the X-band at the positive number 4 vanadium peak.

* * * * *

UNITED STATES PATENT AND TRADEMARK OFFICE
CERTIFICATE OF CORRECTION

PATENT NO. : 5,169,785

DATED : December 8, 1992

INVENTOR(S) : Altman et al

It is certified that error appears in the above-indentified patent and that said Letters Patent is hereby corrected as shown below:

The sheet of drawing consisting of Fig.1, should be deleted and replaced with the sheet of drawing consisting of Fig. 1, as shown on the attached sheet.

Signed and Sealed this

Twenty-eighth Day of December, 1993

Attest:

BRUCE LEHMAN

Attesting Officer     Commissioner of Patents and Trademarks